United States Patent [19]
Misawa

[11] Patent Number: 5,893,844
[45] Date of Patent: Apr. 13, 1999

[54] INDWELLING NEEDLE SET

[75] Inventor: Tojiro Misawa, Tokyo, Japan

[73] Assignee: Misawa Medical Industry Co., Ltd., Tokyo, Japan, JPX

[21] Appl. No.: 08/987,241

[22] Filed: Dec. 9, 1997

[30] Foreign Application Priority Data

Jan. 17, 1997 [JP] Japan ................... 9-017716

[51] Int. Cl.$^6$ .................................................. A61M 5/32
[52] U.S. Cl. ...................... 604/195; 604/164; 604/168; 604/110
[58] Field of Search ....................... 604/164, 168, 604/110, 192, 195, 196, 198, 263

[56] References Cited

U.S. PATENT DOCUMENTS

| | | | |
|---|---|---|---|
| 4,417,887 | 11/1983 | Koshi | 604/162 |
| 4,772,265 | 9/1988 | Walter | 604/164 |
| 4,834,718 | 5/1989 | McDonald | 604/195 |
| 5,403,286 | 4/1995 | Lockwood, Jr. | 604/110 |

*Primary Examiner*—Corrine M. McDermott
*Assistant Examiner*—Cris L. Rodriguez

*Attorney, Agent, or Firm*—Kanesaka & Takeuchi

[57] ABSTRACT

Disclosed is an indwelling needle set comprising a cylinder provided with a flexible outer needle composed of a synthetic resin at the tip thereof and a plunger which is inserted in the cylinder and is provided with a metallic inner needle at the tip thereof, wherein the plunger is provided with a piston which slidingly-contacts the surface of the inside wall of the cylinder, an orifice which opens to the inside of the cylinder in front of the piston, a rear opening formed at the rear end of the cylinder for connecting a connecting tube, and a conduit penetrating through the plunger and connecting the orifice with the rear end opening; and the plunger is inserted into the cylinder in a manner that the piercing position at which the tip of the inner needle projects from the tip of the outer needle is allowed to slide relative to the housing position at which the inner needle is housed after it is backed away. The indwelling needle set has excellent features by which a medicinal solution can be injected and blood can be removed while the inner needle is allowed to remain in the cylinder after it is backed away and a disadvantage caused by the presence of the inner needle within the cylinder, specifically, an increase in flow resistance caused by the passage of a medicinal solution or the like through the inside of a needle tube of the inner needle can be eliminated.

8 Claims, 4 Drawing Sheets

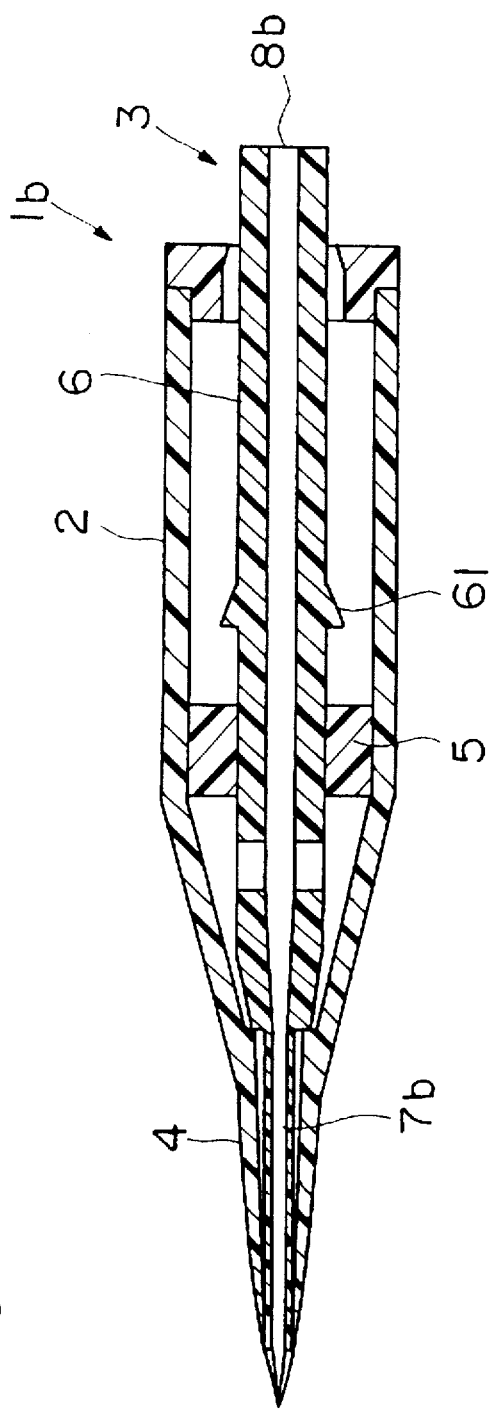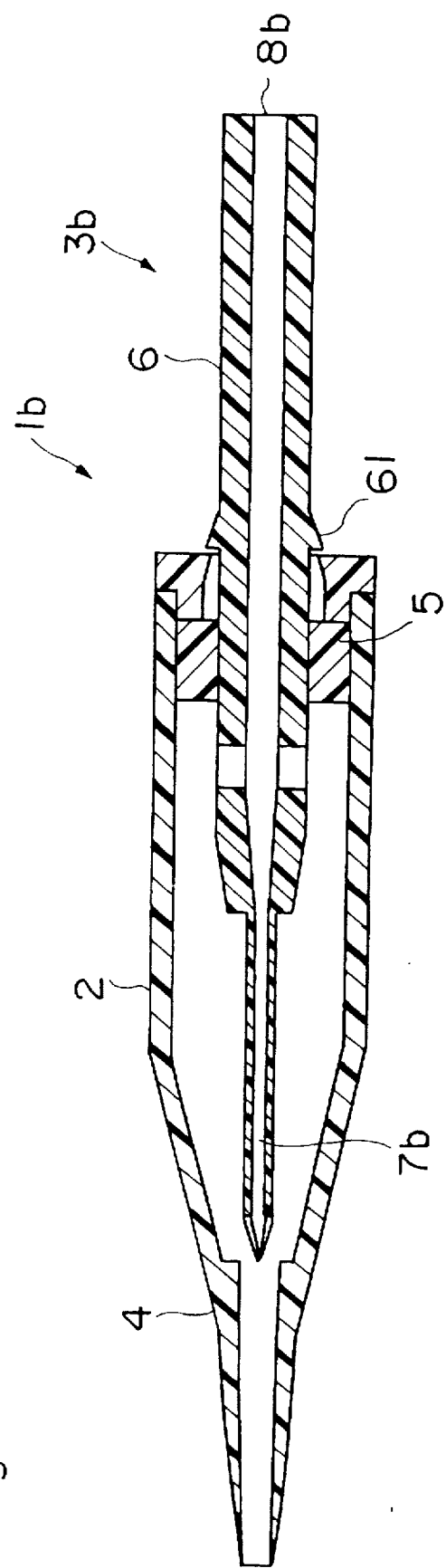

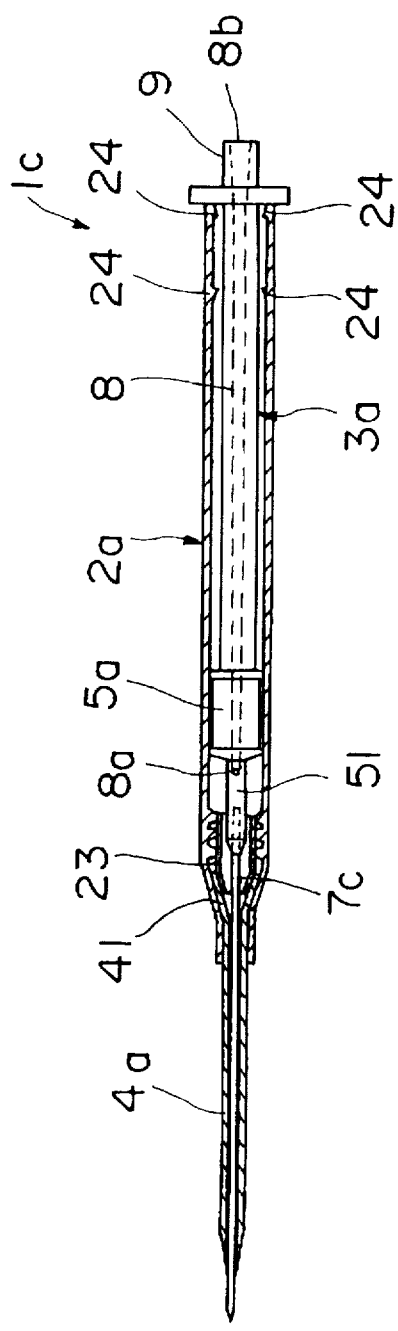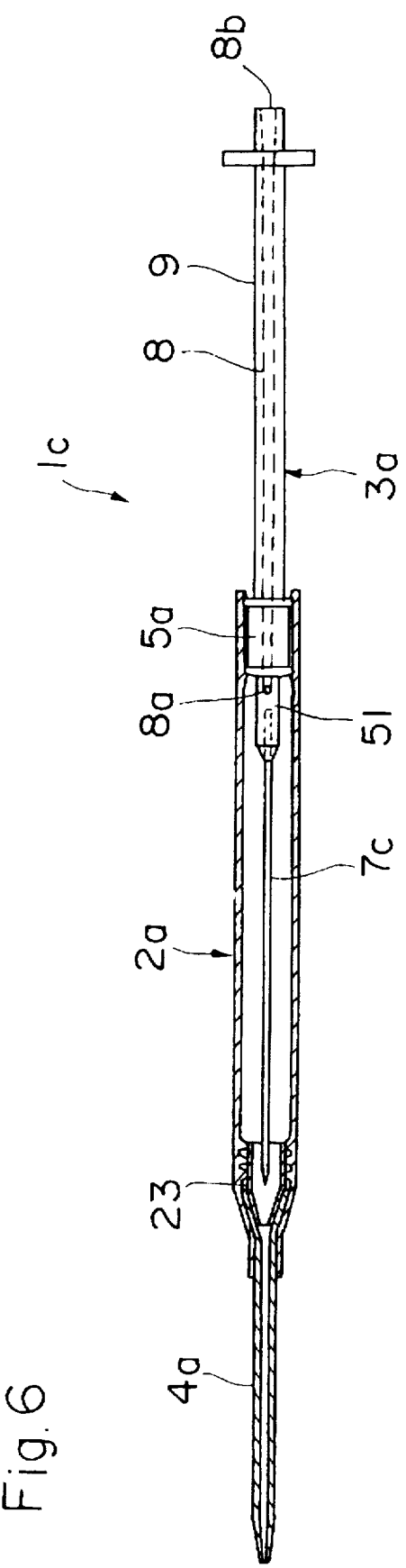

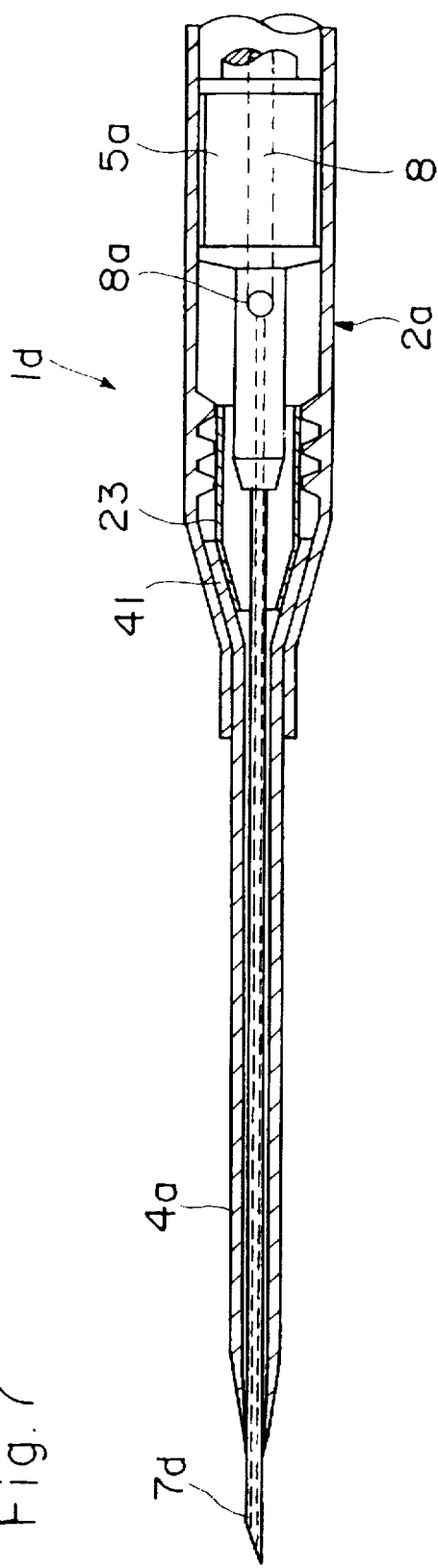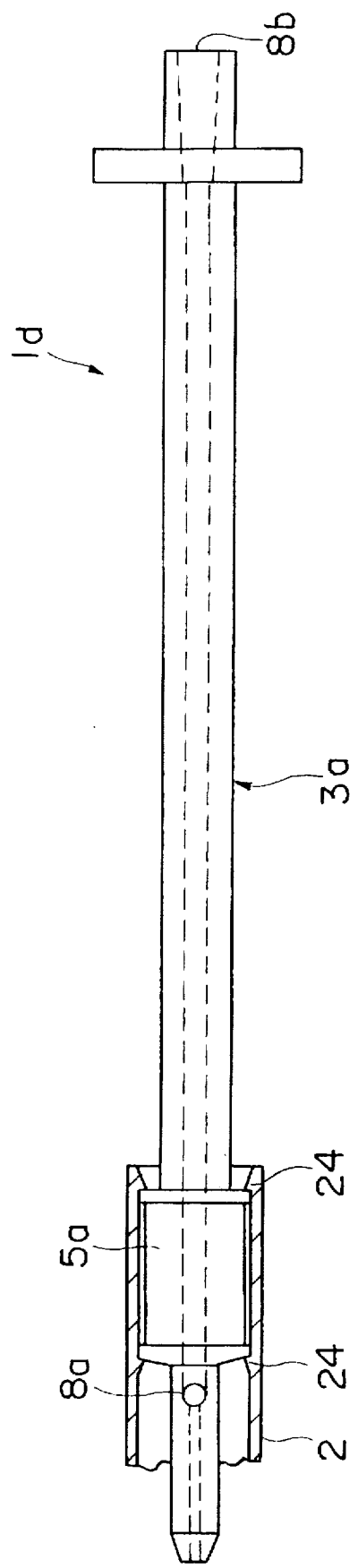

5,893,844

1

INDWELLING NEEDLE SET

BACKGROUND OF THE INVENTION

1. Field of the Invention

This invention relates to a disposable-type indwelling needle set provided with a needle tip composed of a soft synthetic resin.

2. Description of the Related Art

There is a conventionally known indwelling needle set comprising a metallic inner needle, which is provided with a flexible outer needle composed of a synthetic resin, outside the inner needle. A patient is pierced with the tip of the inner needle to insert the tip of the outer needle in a blood vessel together with the inner needle. Then, only the inner needle is removed to connect a connecting tube to the base of the outer needle whereby treatments such as drip infusion or the like are carried out.

However, complicated and careful operations are required for preventing infection and the like to carry out the sequence using the conventional indwelling needle set, in which only the inner needle is removed under such conditions that a blood vessel is pierced with the outer needle and then the connecting tube is connected to the base of the outer needle.

SUMMARY OF THE INVENTION

This invention has been achieved in view of this situation and has an object of providing an indwelling needle set in which an inner needle is allowed to remain in a cylinder by moving it backward and eliminating the work of removing the inner needle without the disadvantage caused by the presence of the inner needle within the cylinder, specifically, without the drawback of an increase in flow resistance caused by the passage of a medicinal solution or the like through the inside of the needle tube of the inner needle.

The above objects can be attained in the present invention by the provision of an indwelling needle set comprising a cylinder provided with a flexible outer needle composed of a synthetic resin at the tip thereof and a plunger. This plunger is inserted into the cylinder and is provided with a metallic inner needle at the tip thereof, wherein the plunger is provided with a piston which slidingly-contacts the surface of the inside wall of the cylinder. An orifice is opened to the cylinder in front of the piston and a rear opening is formed at the rear of the cylinder to be connected to a connecting tube, and a conduit is formed for penetrating through the plunger and connecting the orifice with the rear end opening. The plunger is inserted into the cylinder in a manner that the piercing position at which the tip of the inner needle projects from the tip of the outer needle is allowed to slide relative to the housing position at which the inner needle is housed after it is backed away.

When the indwelling needle set of the present invention is used, the connecting tube is connected with the rear opening of the plunger, the plunger is advanced to the piercing position, and the needle tip of the indwelling needle with a double structure is led by the inner needle tip projecting from the tip of the outer needle whereby a blood vessel is pierced with the needle tip of the indwelling needle. Then, when the plunger is backed off to the housing position, the inner needle is housed in the cylinder and the outer needle serves to connect the blood vessel with the inside of the cylinder. The connecting tube communicates with the inside of the cylinder through the conduit, rear opening, and front orifice, which are formed in the plunger, so that a medicinal

2 solution can be transferred to the blood vessel from the connecting tube via the plunger, cylinder, and outer needle, and blood can be reversely transferred from the blood vessel to the connecting tube.

By these means, the connecting tube can communicate with the blood vessel, while the inner needle remains built-in and hence a conventionally complicated operation for removing the inner needle and connecting the connecting tube with the outer needle can be eliminated. Also, these measures are effective in preventing for infection.

Further, since the inside path of the inner needle is excluded from the flow passage from the connecting tube to the blood vessel, the flow resistance does not increase.

Incidentally, the synthetic resin as used in the present invention includes a synthetic rubber.

BRIEF DESCRIPTION OF THE DRAWINGS

These and other objects and features of the present invention will become clearer by the following description of the present invention made with reference to the accompanying drawings, in which:

FIG. 3 is a sectional view schematically showing a condition of a piercing position of a second embodiment (second example);

FIG. 4 is a sectional view schematically showing a condition of the housed position of the second embodiment (second example);

FIG. 5 is a sectional view schematically showing a condition of a piercing position of a third embodiment (third example);

FIG. 6 is a sectional view schematically showing a condition of the housed position of the third embodiment (third example);

FIG. 7 is an enlarged sectional view of the tip schematically showing a condition of a piercing position of a fourth embodiment (fourth example); and FIG. 8 is an enlarged sectional view of the tip schematically showing a condition of the housed position of the fourth embodiment (fourth example).

DETAILED DESCRIPTION OF THE PREFERRED EMBODIMENTS

Figure 1:
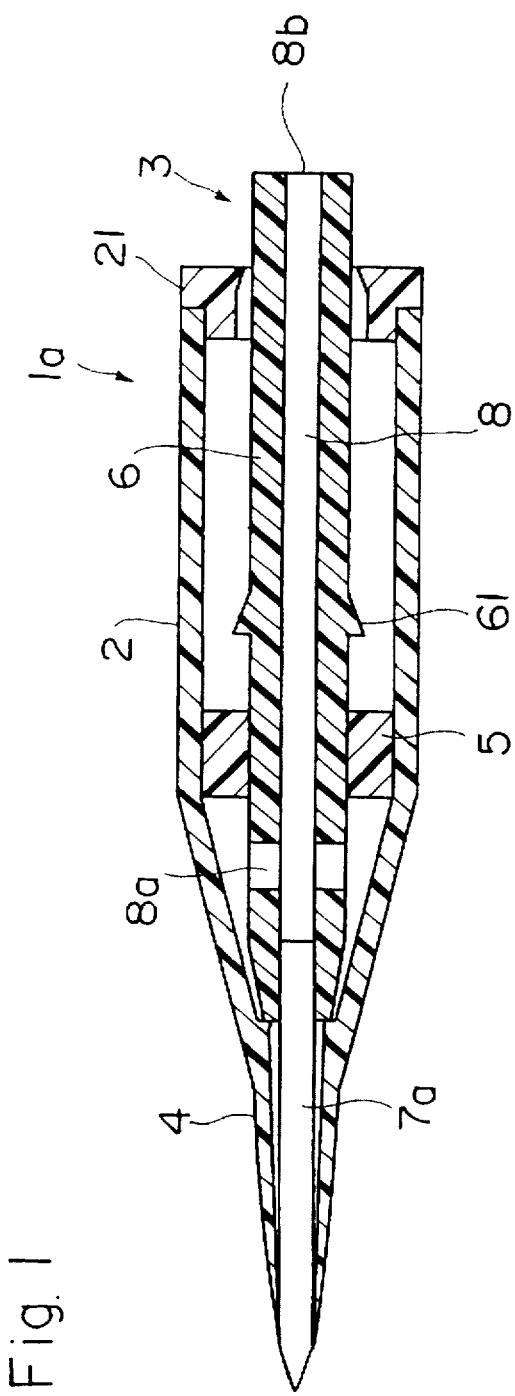
FIG. 1 is a sectional view schematically showing a condition of a piercing position of a first embodiment (first example)

Next, preferred embodiments of the present invention will be described with reference to the drawings.

<First Example>

An indwelling needle set corresponding to a first embodiment is now illustrated with reference to FIGS. 1 and 2.

An indwelling needle set 1a comprises a cylinder 2 composed of a transparent or semi-transparent synthetic resin and a plunger 3 housed in a hollow portion of the cylinder 2 in such a manner that it can be freely moved forward and backward. A sheath pipe 4 (outer needle) is integrally formed at the point of the cylinder 2. A clamping ring 21 made from an elastic synthetic resin is attached to an opening formed at the rear of the cylinder 2. The clamping ring 21 has an inside diameter which is smaller than that of the cylinder 2 and gradually decreases toward the rear.

The plunger 3 is provided with a hollow piston pipe 6 with a point to which a piston 5 is attached. An inner needle 7a made from a solid metal is embedded in the tip point of the plunger 6. The cylinder 2 and the plunger 3 constitute an indwelling needle body. A connecting tube is connected to the rear end of the indwelling needle body, specifically, to the rear end of the piston pipe 6 of the plunger either through or not through an appropriate connector and/or a shut-off cock, although these parts are not shown.

The cylinder 2 and the plunger 3 are assembled so that they can relatively slide from a piercing position shown in FIG. 1, at which the tip of the inner needle 7a projects from the point of the sheath pipe 4, to the housing position at which a flow passage for a medicinal solution and the like is formed between the tip of the inner needle 7a and the sheath pipe 4 and between the inner needle 7a and the inside wall of the cylinder 2. The hollow portion of the piston pipe 6 of the plunger 3 forms a conduit 8 passing along the axes of the plunger and communicates with the inside of the cylinder 2 via an orifice 8a drilled through the piston pipe 6 at a position nearer to the point of the piston pipe 6 than the piston 5. The rear end of the piston pipe 6 is opened to form a rear opening 8b communicating with a connecting tube (not shown).

A projection 61 is formed in the center of the piston pipe 6 at the rear of the piston 5. The projection 61 forms a taper spreading from the rear to the front of the piston pipe 6 and cooperates with the clamping ring 21 to constitute a clamping structure, thereby hindering the re-advancing of the plunger which has been backed to the housing position Next, the action of the indwelling needle set corresponding to the first embodiment will be explained.

The needle tip of the indwelling needle with a double structure is led by the tip of the inner needle 7a projecting from the point of the sheath pipe 4 at the piercing position shown in FIG. 1 so that it is allowed to penetrate a blood vessel, then the plunger 3 is slightly backed away and the flashback from the blood vessel is confirmed.

Figure 2:
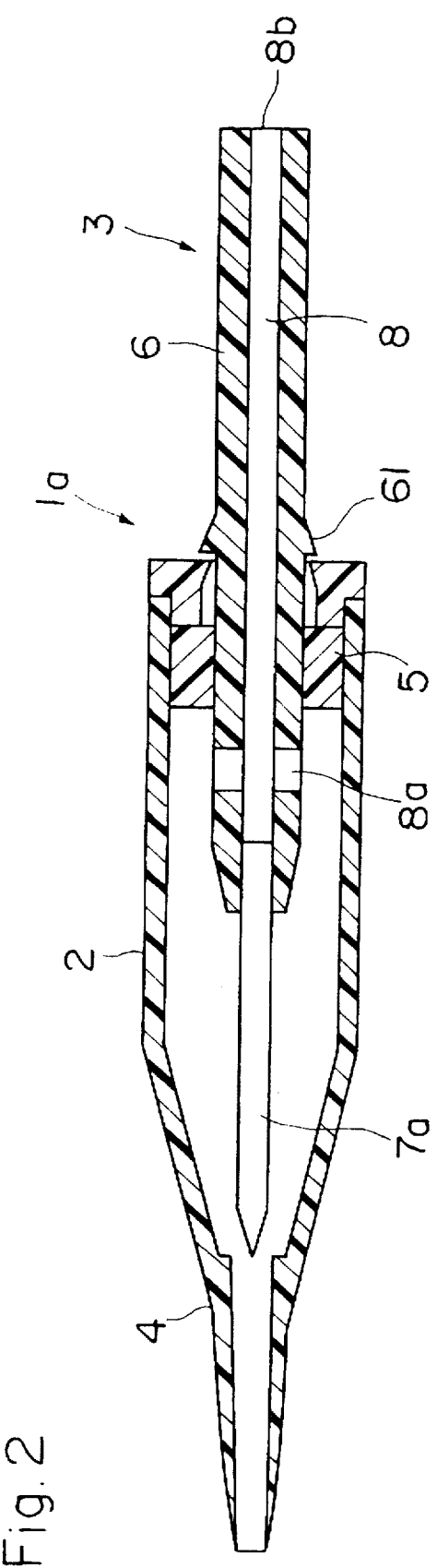
FIG. 2 is a sectional view schematically showing a condition of the housed position of the first embodiment. (first example)

Then, when the plunger is entirely backed off to the housing position as shown in FIG. 2, the projection 61 is allowed to cross over the clamping ring to reach the rear side of the clamping ring due to the elastic deformation of the clamping ring 21 of the cylinder, whereby the re-advancing of the plunger 3 is prevented. At the same time, when the plunger is backed off to the housing position, the piston 5 directly contacts the front end of the clamping ring 21 whereby the retreat of the plunger 3 is prevented so that the plunger 3 is secured to the cylinder 2 at the housing position.

In this state, the inner needle 7a is backed away to the inside of the cylinder 2 and housed in the cylinder 2 and the hollow portion of the clamping pipe 4 communicates with the inside of the cylinder 2 with the blood vessel. The sheath pipe 4 communicates with the rear opening 8b of the plunger 3 via the conduit 8 of the piston pipe 6, the orifice 8a of the piston pipe 6, a clearance between the piston pipe 6 and the inner wall of the cylinder 2, and a space clearance of the cylinder 2.

As a result, as opposed to conventional indwelling needle sets, the indwelling needle set corresponding to this embodiment requires no operation for connecting a connecting tube with a sheath pipe after removing an inner needle, hence it is more simplified in operation than the conventional set. Particularly, because blood never leaks externally, it serves to prevent pestiferous infections which are acquired through blood infection. Also, since the inside of the needle pipe of the inner needle is excluded from the flow passage, an increase in flow resistance in the sheath pipe can be prevented thereby reducing the stress on the patient that much more during an operation.

<Second Example>

An indwelling needle set corresponding to a second embodiment is now illustrated with reference to FIGS. 3 and 4.

An indwelling needle set 1b of this embodiment is basically the same as that of the first embodiment except that an inner needle 7b imbedded in the point of a piston pipe 6 has the same hollow structure as a usual needle. Therefore, in FIGS. 3 and 4, the same parts as in FIGS. 1 and 2 are represented by the same symbols and detailed explanations will be omitted.

When the indwelling needle set 1b of the second embodiment is used, the needle tip of the indwelling needle with a double structure is led by the tip of the inner needle 7b projecting from the point of a sheath pipe 4 at the piercing position shown in FIG. 3 so that it is allowed to penetrate a blood vessel and the flashback from the blood vessel is confirmed. In this case, the flashback can be confirmed faster than in the first embodiment since blood flows into a plunger 3 immediately from the hollow inner needle 7b.

Then, the plunger 3 is backed away to the housing position as shown in FIG. 4, a clamping ring 21 is allowed to clamp a projection 61 to communicate with the rear end of the plunger 3 with the point of a sheath pipe, whereby operations for injecting a medicinal solution into a blood vessel from a connecting tube connected with the rear end of the plunger 3 and for removing blood from the blood vessel to the connecting tube can be performed.

<Third Example>

An indwelling needle set corresponding to a third embodiment is now illustrated with reference to FIGS. 5 and 6.

FIG. 7 is an enlarged view of the point at a piercing position and FIG. 8 is an enlarged view of the rear portion at the housing position although the configuration of an inner needle is different.

In an indwelling needle set 1c of the third embodiment, a cylinder 2a and an outer needle 4a are separately formed. The separate outer needle 4a composed of a transparent or semi-transparent flexible synthetic resin such as polyurethane, a vinyl chloride resin, or the like is attached to the cylinder head of the cylinder 2a composed of a transparent or semi-transparent resin. Specifically, the outer needle 4a is provided with a needle pipe of a flexible resin with a thin needle tip formed at one end thereof and with a needle base 41 spreading like a cone at the other end. A bushing 23 made from stainless steel having a shape corresponding to that of the inside of the spread needle base 41 is attached to the point of the cylinder 2a. The bushing 23 is engaged with the needle base 41 of the outer needle 4a by pressure whereby the needle base 41 of the outer needle 4a is secured to the cylinder head of the cylinder 2a.

A plunger 3a, which is disposed in such a manner that it is freely moved forward and backward in the space of the cylinder 2a, is provided with a piston 5a in the center thereof. A projection 51 made from a synthetic resin is secured to the top of the piston 5a. A solid inner needle 7c is imbedded in and secured to the point of the projection 51. A separate piston rod 9 for sliding the piston 5a forward and backward, which is made from a flexible resin and has a hollow structure, is connected and secured to the rear side of the piston 5a.

A conduit 8 penetrating through the central portions of the piston 5a, piston rod 9, and projection 51 of the plunger is formed in the direction of the axes of these. One of the ends of the conduit 8 communicates with an orifice 8a which is formed in the projection 51 at a position nearer to the end than the piston 5a and is opened to the inside of the cylinder 2a, and the other end communicates with the rear opening 8b of the piston rod 9.

The cylinder 2a and the plunger 3a are combined in the same manner as in a conventionally known injection to constitute the body of the indwelling needle set of the present invention. A connecting tube is connected to the rear end of the indwelling needle body, specifically, to the rear opening 8b of the piston rod of the plunger 3a through an appropriate connector and/or a shut-off cock, although these parts are not shown, in the same manner as in conventional indwelling needle set. The cylinder 2a and the plunger 3a are assembled so that they can slide relatively from a piercing position, at which the tip of the inner needle 7c projects from the tip of the outer needle 4a, to the housing position to which the plunger 2a is backed away. Also, a pair of clamping projections 24 (see FIG. 8 for more precise understanding) is formed on the inside wall of the rear portion of the cylinder 2a. The piston 5a is sandwiched between the pair of clamping projections 24 to secure the plunger 3a to the housing position thereby preventing the plunger 3a from backing beyond the housing position and preventing the re-advancing of the plunger 3a backed off to the housing position.

Next, the action of the indwelling needle set according to the third embodiment is now explained.

The needle tip of the indwelling needle with a double structure is led by the tip of the inner needle 7c projecting from the tip of the outer needle 4a at the piercing position shown in FIG. 5 so that it is allowed to penetrate away a blood vessel and the plunger 3a is slightly backed away to confirm the flashback from the blood vessel via the transparent or semi-transparent outer needle 4a.

Then, when the plunger 3a is entirely backed off to the housing position as shown in FIG. 6, the piston 5a is positioned in the center between the pair of projections 24, whereby the re-advancing and slipping out of the plunger 3a are prevented. In this state, the inner needle 7c is backed to the inside of the cylinder and housed in the cylinder. In this case, the tip of the needle is protected by the bushing 23. The tip of the outer needle 4a communicates with the rear opening 8b of the plunger 3a via the conduit 8.

Therefore, as opposed to from conventional indwelling needle sets, the indwelling needle set corresponding to this embodiment requires no operation for connecting a connecting tube with an outer needle after removing an inner needle and hence it is more simplified in operation than the conventional set. Particularly, it serves to prevent pestiferous infections which are acquired through blood infection. Also, an increase in flow resistance due to the passage through the inside of an inner needle can be prevented, thereby reducing the stress on the patient that much more during an operation.

<Fourth Example>

An indwelling needle set corresponding to a fourth embodiment is now illustrated with reference to FIGS. 7 and 8.

FIG. 7 is an enlarged view of only the tip at a piercing position and FIG. 8 is an enlarged view of only the rear portion at the housing position.

An indwelling needle set of the fourth embodiment is basically the same as that of the third embodiment except that an inner needle 7d embedded in the point of a plunger has the same hollow structure as a usual needle. Therefore, in FIGS. 7 and 8, the same parts as in the third embodiment are represented by the same symbols and detailed explanations will be omitted.

When the indwelling needle set of the fourth embodiment is used, the needle tip of the indwelling needle with a double structure is led by the tip of the inner needle 7d projecting from the tip of an outer needle 4a at the piercing position shown in FIG. 7 so that it is allowed to penetrate a blood vessel to view transit of blood through the inside of the inner needle and thereby to confirm the flashback from the blood vessel. In this case, the flashback can be confirmed faster than in the third embodiment since it can be viewed directly after the blood vessel is pierced with the inner needle 7d.

Then, the plunger 3a is backed off to the housing position as shown in FIG. 8 to clamp the plunger 3 and thereby to allow the rear end of the plunger 3a to communicate with the tip of the outer needle 7d, whereby operations for injecting a medicinal solution into a blood vessel from a connecting tube connected with the rear end of the plunger 3a and for removing blood from the blood vessel to the connecting tube can be performed.

In these embodiments 3 and 4, although the outer needle is engaged with and secured to the cylinder using the metallic bushing, it may be secured using an adhesive without using the metallic bushing. Also, it may be mounted in a freely dismountable manner using a known method which is used as a means of binding an injection needle with an injection cylinder.

Numerous modifications and variations of the present invention are possible in light of the above teachings. It is therefore to be understood that, within the scope of the appended claims, the present invention can be practiced in a manner other than as specifically described herein.

What is claimed is:

1. An indwelling needle set comprising a cylinder having an inside wall and a rear end provided with a flexible outer needle having a tip composed of a synthetic resin at the tip thereof and a plunger having a tip which is inserted in the cylinder and is provided with a metallic inner needle at the tip thereof, wherein;

the plunger is provided with a piston which slidingly-contacts the surface of the inside wall of the cylinder, an orifice which is opened to the cylinder in front of the piston, a rear opening formed at the rear end of the cylinder for connecting a connecting tube, and a conduit penetrating through the plunger and connecting the orifice with the rear opening; and the plunger is inserted in the cylinder in such a manner that the piercing position at which the tip of the inner needle projects from the tip of the outer needle is allowed to slide relative to the housing position at which the inner needle is housed after it is backed off.

2. The indwelling needle set according to claim 1, further comprising a clamping structure for securing the positions of the plunger and the cylinder at the housing position.

3. The indwelling needle set according to claim 1, wherein the cylinder and the outer needle are integrally formed in a body.

4. The indwelling needle set according to claim 1, wherein the cylinder and the outer needle are separately formed.

5. The indwelling needle set according to claim 4, wherein the outer needle is provided with a needle pipe having a rear end spreading like a cone;

a metallic bushing having a shape corresponding to that of the inside of the rear end of the needle pipe is attached to the cylinder; and the rear end of the outer needle is engaged with the bushing to secure the outer needle to the cylinder.

6. The indwelling needle set according to claim 4, wherein the plunger is provided with a piston rod and the conduit penetrates through the piston and the piston rod.

7. The indwelling needle set according to claim 1, wherein the inner needle has a solid structure.

8. The indwelling needle set according to claim 1, wherein the inner needle has a hollow structure.

* * * * *